United States Patent [19]

Mase et al.

[11] Patent Number: 4,559,126
[45] Date of Patent: Dec. 17, 1985

[54] ELECTROCHEMICAL DEVICE

[75] Inventors: Syunzo Mase, Aichi; Shigeo Soejima, Nagoya, both of Japan

[73] Assignee: NGK Insulators, Ltd., Japan

[21] Appl. No.: 635,739

[22] Filed: Jul. 30, 1984

[30] Foreign Application Priority Data

Aug. 9, 1983 [JP] Japan .............................. 58-144475

[51] Int. Cl.⁴ .......................................... G01N 27/56
[52] U.S. Cl. ................................... 204/425; 204/426
[58] Field of Search ............... 204/425, 426, 1 S, 427, 204/428, 429

[56] References Cited

U.S. PATENT DOCUMENTS 4,334,974  6/1982  Muller et al. ................ 204/425
4,399,017  8/1983  Inoue et al. ................. 204/425
4,416,763 11/1983  Fujishiro .................... 204/412

Primary Examiner—G. L. Kaplan
Attorney, Agent, or Firm—Parkhurst & Oliff

[57] ABSTRACT

In an electrochemical device having an electrochemical cell with electrodes mounted on a solid electrolyte layer and a heater carried by a ceramic high-electric layer, a resistance ceramic layer is disposed between the solid electrolyte layer and the ceramic layer.

23 Claims, 4 Drawing Figures

FIG_2

ELECTROCHEMICAL DEVICE

BACKGROUND OF THE INVENTION

1. Field of the Invention

This invention relates to an electrochemical device which has excellent low-temperature performance and is easy to miniaturize. More particularly, the invention relates to an electrochemical device having a heater to heat a solid electrolyte thereof.

2. Description of the Prior Art

As an example of electrochemical devices using a solid electrolyte, an oxygen sensor for detecting the oxygen concentration of automobile exhaust gas has been used heretofore. To ensure proper operation of the oxygen sensor when the exhaust gas temperature is comparatively low, it has been known to attach a heater to the sensor; for instance, by inserting a heater in a hole of a cylindrical zirconia solid electrolytic cell having one end thereof closed, or attaching a heater, made of a resistive heating element buried in an alumina porcelain, to one side surface of a planar zirconia solid electrolyte cell.

However, the electrochemical device of the prior art has shortcomings in that its assembly structure is so complicated that the device tends to become large, and that, due to the difference in thermal expansion or sintering shrinkage between insulator portion and solid electrolyte portion thereof, the insulator portion and solid electrolyte portion are susceptible to cracks, resulting in a poor reliability.

SUMMARY OF THE INVENTION

Therefore, a first object of the present invention is to provide a highly reliable electrochemical device of unitary structure. To this end, ceramics of the electrochemical device are prevented from cracking by reducing the difference of thermal expansion between an electrochemical cell and a heater layer thereof.

A second object of the present invention is to provide a highly accurate electrochemical device of unitary structure. To this end, the insulation between an electrochemical cell and a heater is improved.

A third object of the present invention is to provide a highly reliable electrochemical device of unitary structure by bringing about a coincidence of sintering shrinkage between an electrochemical cell and a heater layer thereof so as to prevent the occurrence of cracks in ceramics therein.

To fulfill the above-mentioned objects, an electrochemical device according to the present invention comprises an electrochemical cell having at least one pair of electrodes disposed in contact with a solid electrolyte, a heater layer having a heater carried by a ceramics layer with substantially the same coefficient of thermal expansion as that of said solid electrolyte, and a high-electric resistance ceramics layer spread substantially over the entire span between said solid electrolyte and said ceramics layer so as to be attached to both said solid electrolyte and said ceramics layer.

In a preferred embodiment of the electrochemical device of the invention, the solid electrolyte and the ceramics layer contain zirconia ($ZrO_2$) as a major ingredient thereof, while the high-electric resistance ceramics layer is made of porous alumina or spinel. However, the invention is not restricted by such ingredients.

BRIEF DESCRIPTION OF THE DRAWINGS

For a better understanding of the invention, reference is made to the accompanying drawings, in which.

Throughout different views of the drawings, 1, 3, 4 are solid electrolyte layers, 2, 5 are electrodes, 7, 29 are porous ceramics layers, 6 is a hollow cavity, 8, 9, 30 are ceramics layers, 10 is a heater, 11 is a terminal, 12 is a high-electric resistance ceramics layer, 13 is a housing, 14, 16 are openings, 15 is a heat-insulating cylinder, 17 is a cap, 18 is a venthole, 19 is an insulator, 20 is a hole, 21 is a flange, 22 is a glass layer, 23 is a sealing portion, 24 is a spring, 25 is a washer, 26 is a DC power source, 27 is a voltmeter, 31, 32 are porous high-electric resistance ceramics layers, 33 is a porous solid electrolyte layer, and 34 is a resistance.

DESCRIPTION OF THE PREFERRED EMBODIMENTS

Figure 1:
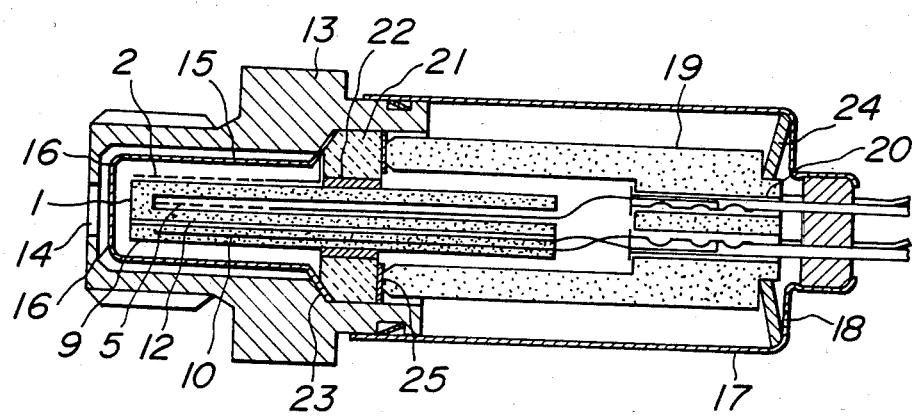
FIG. 1 is a schematic sectional view of a practicable oxygen concentration sensor embodying the electrochemical device according to the present invention.
Figure 2:
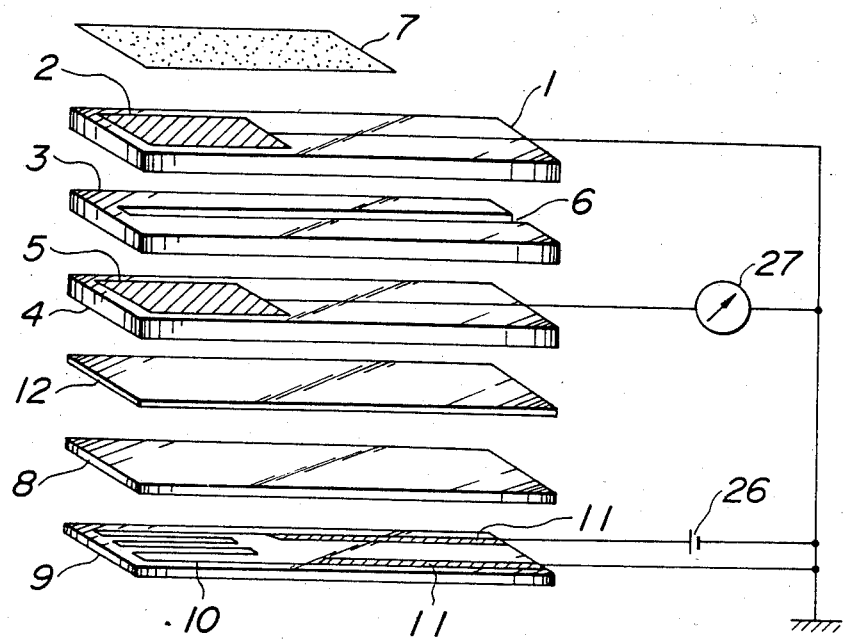
FIG. 2 is an explanatory diagram showing a schematic exploded view of the essential portion of the oxygen concentration sensor of FIG. 1 while indicating the electric connections therein.

The details of the electrochemical device of the invention will be described now by referring to FIG. 1 showing an oxygen concentration sensor embodying the invention and FIG. 2 showing an exploded view of the essential portion thereof.

A solid electrolyte layer 1 is, for instance, made of yttria-added zirconia porcelain, and an electrode 2 made of a porous platinum layer is disposed on one side surface of the solid electrolyte layer 1. An intermediate solid electrolyte layer 3 and another solid electrolyte layer 4 carrying an electrode 5 are attached to the opposite side surface of the solid electrolyte 1, so as to form an electrochemical cell acting as an oxygen concentration cell. The material of the two solid electrolyte layers 3 and 4 is the same as that of the solid electrolyte layer 1. A porous spinel layer 7 is deposited on the electrode 2 by plasma spray coating, so that the electrode 2 is exposed to a gas being measured through the thus deposited porous spinel layer 7. The other electrode 5 faces a hollow cavity 6 surrounded by the solid electrolyte layers 1, 3, and 4.

Two ceramics layers 8 and 9, both having substantially the same coefficient of thermal expansion as that of the solid electrolyte layers 1, 3, and 4, hold a heater 10 and the terminals 11 airtightly embedded therebetween. The material of the heater 10 and the terminals 11 consists of 70% by weight of platinum, 10% by weight of rhodium, and 20% by weight of alumina powder. A high-electric resistance ceramic layer 12 is disposed between the solid electrolyte layer 4 and the ceramics layer 8 so as to be attached to both the solid electrolyte and ceramic layers, whereby, an electrochemical device embodying the invention is formed.

The gas being measured reaches the surface of the electrode 2 after passing through the opening 14 of a housing 13 and the opening 16 of a heat-insulating cylinder 15. Reference gas or air reaches the electrode 5 acting as a reference electrode after passing through the venthole 18 of a cap 17 and the hole 20 of an insulator 19. The gas being measured is gastightly separated from the air or the reference gas by a combination of a supporter flange 21, a glass layer 22, and a sealing portion 23. The glass layer 22 is filled between the supporter flange 21 and the abovementioned electrochemical device, which device has the solid electrolyte layers 1, 3, and 4, the ceramics layers 8 and 9, and the high-electric resistance ceramic layer 12. The sealing portion 23 is urged against the supporter flange 21 or the housing 13 by a spring 24 through the insulator 19 and a washer 25 made of metal or other suitable material, so as to ensure gastightness at the junction between the supporter flange 21 and the housing 13.

When the terminals 11 of the heater 10 are connected to a DC power source 26, an electric current is applied to the heater 10 so as to produce Joule heat from the heater 10. The Joule heat acts to heat up various layers in contact with the heater 10 directly or indirectly; namely, the solid electrolyte layers 1, 3 and 4, the high-electric resistance ceramic layer 12, and the ceramics layers 8 and 9.

With the temperature rise, the ceramic layers 8 and 9 become increasingly conductive. When the ceramic layers 8 and 9 become sufficiently conductive, a portion of the DC current applied to the heater 10 leaks to the ceramic layers 8 and 9. However, the high-electric resistance ceramic layer 12 electrically insulates the solid electrolyte layers 1, 3, and 4 from the ceramic layers 8 and 9, so that the current leaked from the heater 10 is restricted only to the ceramic layers 8 and 9 and no detrimental effects result on the performance of the electrochemical cell by such leakage.

The coefficient of thermal expansion of the ceramic layers 8 and 9 is required to be substantially the same as that of the solid electrolyte layers 1, 3, and 4, and the difference between the former coefficient and the latter coefficient is preferably smaller than $1 \times 10^{-6}/K$. For instance, when the solid electrolyte layers 1, 3, and 4 are made of zirconia porcelain mainly consisting of tetragonal phase with a composition of 97 mol % of zirconia ($ZrO_2$) and 3 mol % of yttria ($Y_2O_3$), the ceramic layers 8 and 9 may be made of zirconia porcelain with the same composition or zirconia porcelain having a high electric resistance and mainly consisting of tetragonal phase with a composition of 79 mol % of zirconia ($ZrO_2$), 10 mol % of yttria ($Y_2O_3$), and 11 mol % of niobium oxide ($Nb_2O_3$). The high electric resistance of the ceramic layers 8 and 9 reduces the leakage of electric current from the heater 10.

The high-electric resistance ceramic layer 12 can be made of a ceramic having a high electric resistance at high temperatures, such as ceramics mainly consisting of alumina, spinel, borosilicate glass, mullite, and the like. Since the high-electric resistance ceramic layer 12 is inserted between layers having substantially the same coefficient of thermal expansion, the high-electric resistance ceramic layer 12 seldomly delaminates from the solid electrolyte layer 4 even if there is a difference in thermal expansion between them. The thickness of the high-electric resistance ceramic layer 12 is perferably less than 100 $\mu$m, more preferably less than 50 $\mu$m.

To reduce further the stress due to the difference of thermal expansion therebetween, the high-electric resistance ceramic layer 12 can be made porous, and in this case the risk of delamination is further reduced. As another means for reducing the thermal stress, a layer of mixed composition may be disposed either between the high-electric resistance ceramic layer 12 and the solid electrolyte layer 4 or between the high-electric resistance ceramic layer 12 and the ceramic layer 8. The gradual change of the composition provided by such a mixed composition has been found effective in reducing the thermal stress.

As a typical method of forming the high-electric resistance ceramic layer 12, a paste of ceramic material particles for the high-electric resistance ceramic layer is printed on a green body of the solid electrolyte layer 4, and materials for the ceramic layer 8, the heater 10, and the ceramic layer 9 are printed thereon in succession, and then the green body with the thus printed layers is sintered. Alternatively, a board consisting of the ceramic layers 8, 9 and the heater 10 is pre-sintered, and the high-electric resistance ceramic layer is formed on the surface of the board by vacuum evaporation, sputtering, paste baking, plasma spray coating, or the like, and then the solid electrolyte layers and the electrodes are formed thereon by sputtering or printing of green body followed by sintering.

As to the material of the heater 10, from the standpoint of durability, refractory metals, such as nickel, silver, gold, platinum, rhodium, palladium, iridium, ruthenium, tungsten, molybdenum, and the like and alloys thereof are preferable. Besides, compounds such as zinc oxide (ZnO), lanthanum chromite ($LaCrO_3$), lanthanum boride ($LaB_6$), silicon carbide (SiC), and the like can be also used for the heater 10. Preferably, fine powder particle of zirconia, yttria, alumina, or the like is mixed in the heater, so as to prevent delamination or breakage of the heater 10 due to sintering caused during the use thereof.

Figure 3:
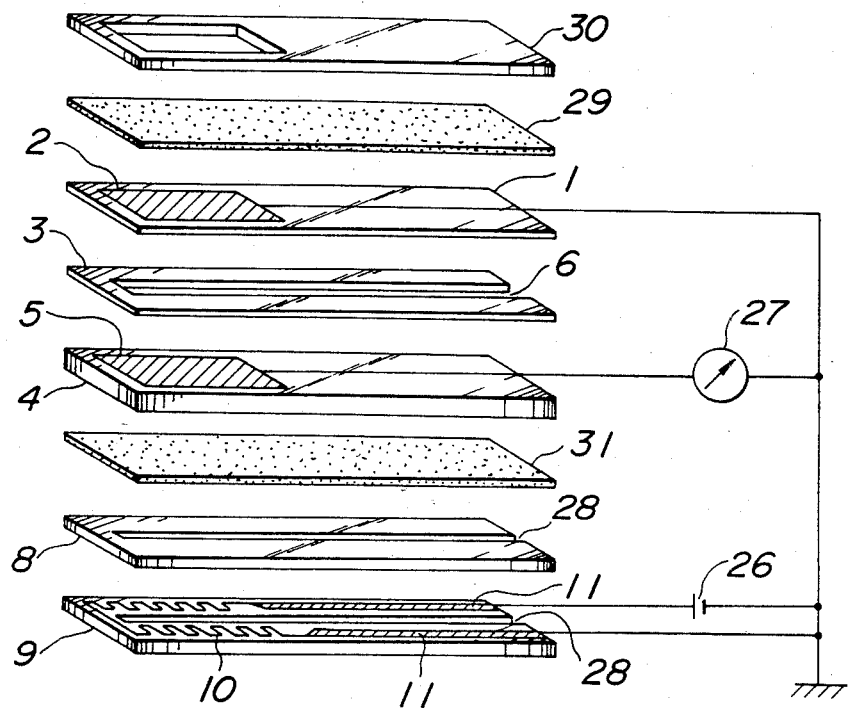
FIG. 3 is a schematic exploded view of the essential portion of another embodiment of the electrochemical device according to the present invention.

Preferably, the shape of the ceramic layers 8 and 9 is such that they shield the heater 10 from the gas being measured. When a direct current is applied to the heater 10 from the DC power source 26 with uniform polarity, the ceramic layers 8 and 9 may be protected from deterioration due to the leakage current by forming a gap 28 in them between those portions where mutually facing portions of the heater 10 are located, as shown in FIG. 3. If such gap 28 is provided, the direct current can be applied to the heater 10 without causing any deterioration of the ceramic layers 8 and 9 even when the electric resistance of such ceramic layers is low at high temperature.

The solid electrolyte to be used in the present invention can be not only the above-mentioned zirconia porcelain but also $\beta$-alumina, aluminum nitride, NASICON, strontium cerium oxide ($SrCeO_8$), solid solution of bismuth oxide ($Bi_2O_3$)-oxide of rare earth element, $La_{1-x}Ca_xYO_{3-y}$. The electrochemical cell to be used in the present invention is not restricted to a concentration cell, but it can be an electrochemical pump, an electrolytic cell of the limiting diffusion current method, and the like.

The electric current to be applied to the heater 10 is not restricted to a direct current, but it can be an alternating current, or a pulse current.

Referring to FIG. 3, to prevent the electrochemical device of the invention from warping during sintering, for instance, a green body layer for a porous ceramic layer 29 of the same material as that of the high-electric resistance ceramic layer 31 and another green body layer for a ceramic layer 30 of the same material as that of the ceramic layers 8, 9 are laid on that side of the solid electrolyte layer 4 which is opposite to the heater 10 before sintering, as shown in the figure. Then, the entire layers including the solid electrolyte layer and the ceramics layers laid thereon are sintered.

The invention will be described in further detail by referring to examples.

EXAMPLE 1

A body was prepared by mixing 100 parts by weight of powder material containing 97 mol % of zirconia ($ZrO_2$) and 3 mol % of yttria ($Y_2O_3$), 1 part by weight of alumina as a sintering aid, 8 parts by weight of polyvinyl butyral and 4 parts by weight of dioctyl phthalate as binder, and 60 parts by weight of trichloroethylene as a solvent. The body was shaped and dried to produce a 1 mm thick solid electrolyte layer 4 as shown in FIG. 3.

On the one side of the solid electrolyte layer 4 thus prepared, the following heater side layers were printed. Namely, a porous high-electric resistance ceramic layer 31 with a thickness of 30 $\mu$m was printed on that side surface of the solid electrolyte layer 4 by the screen printing of a paste made of a powder material consisting of 98% by weight of alumina ($Al_2O_3$), 1.5% by weight of silica ($SiO_2$), and 0.5% by weight of calcia (CaO), and a binder. A ceramic layer 8 with a thickness of 70 $\mu$m having a gap was printed on the high-electric resistance ceramic layer 31 by the screen printing of a paste made of a powder material consisting of 79 mol % of zirconia ($ZrO_2$), 10 mol % of yttria ($Y_2O_3$), and 11 mol % of niobium oxide ($Nb_2O_3$), and a binder. A heater 10 with terminals 11 was printed on the ceramic layer 8 by using a paste made of a heater material consisting of 80 weight % of platinum powder and 20 weight % of alumina powder and a binder. Further, a ceramic layer 9 was printed on the heater by using the same material as that of the ceramic layer 8.

On the opposite side of the solid electrolyte layer 4, the following cell side layers were printed. Namely, an electrode 5 was printed by using a mixture consisting of 90 weight % of platinum powder and 10 weight % of zirconia powder. A 100 $\mu$m thick solid electrolyte layer 3 having a hollow cavity 6 was printed on that side surface of the solid electrolyte layer 4 with the electrode 5 by using the same material as that of the layer 4. Then, a 100 $\mu$m thick solid electrolyte layer 1 with the same chemical composition as that of the solid electrolyte layer 4, another electrode 2 with the same chemical composition as that of the electrode 5, a 30 $\mu$m thick porous ceramic layer 29 with the same chemical composition as that of the porous high-electric resistance ceramic layer 31, and a 100 $\mu$m thick ceramic layer 30 with the same chemical composition as that of the ceramic layer 8 were printed on the solid electrolyte layer 3 in succession as shown in FIG. 3. The thus printed combination of the layers was baked at 1,400° C. in air, and an oxygen concentration sensor was prepared.

A 14 V DC power source 26 was connected across the two terminals 11 of the heater 10 of the oxygen concentration sensor, so as to apply an electric current thereto. In one minute after the connection, the temperature of the solid electrolyte layer 1 was raised to 500° C. The oxygen concentration sensor was placed in an automobile exhaust gas of 200° C., and the electromotive force across the electrode 2 and the electrode 5, representing the oxygen concentration of the exhaust gas or the concentration of an electrode-reaction-sensitive component of the gas being measured, was determined by a voltmeter 27. It was 750 mV in an exhaust gas with an air-fuel ratio $\lambda$ of 0.95, and 65 mV in an exhaust gas with $\lambda = 1.05$. The output voltage across the electrodes 2 and 5 was the same when the DC power source 26 was replaced with a 14 V power source, and said output voltage was not deteriorated even after continuous running of 800 hours in said exhaust gas.

The coefficient of thermal expansion of the zirconia porcelain forming the solid electrolyte layers 1, 3, and 4 was $10.6 \times 10^{-6}$/K over 40°–800° C., while the corresponding coefficient of thermal expansion of the porcelain forming the ceramic layers 8, 9, and 30 was $10.2 \times 10^{-6}$/K over 40°–800° C. The electric volume resistivity of said zirconia porcelain was $2.2 \times 10^3$ $\Omega$·cm at 600° C., while the electric volume resistivity of said porcelain was $2.4 \times 10^7$ $\Omega$·cm at 600° C.

EXAMPLE 2

Figure 4:
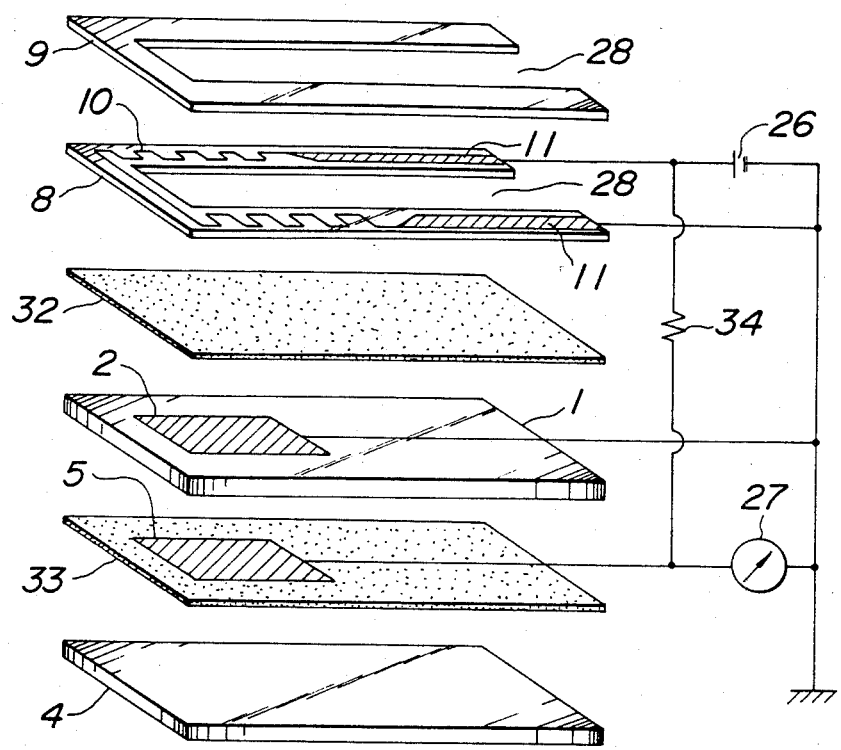
FIG. 4 is a view similar to FIG. 3, showing the essential portion of a different embodiment of the invention together with electric connections therein.

Referring to FIG. 4, a 0.3 mm thick solid electrolyte layer 4 was prepared by using a zirconia green body made of 100 parts by weight of a powder material consisting of 92 mol % of zirconia ($ZrO_2$) and 8 mol % of ytterbium oxide ($Yb_2O_3$), 0.5 part by weight of clay as a sintering aid, and the same binder as those of Example 1. A porous solid electrolyte layer 33 of the same chemical composition and an electrode 5 with a chemical composition of 90 weight % of platinum and 10 weight % of zirconia ($ZrO_2$) were laid on the solid electrolyte layer 4 in said order.

Further, a 0.3 mm thick solid electrolyte layer 1 with the same chemical composition as said zirconia green body, another electrode 2 with the same chemical composition as the electrode 5, a porous alumina ceramic layer 32, ceramic layers 8 and 9 of the same composition as that of the solid electrolyte layer 4, and a heater 10 with terminals 11 with a chemical composition of 70 weight % of platinum powder, 10 weight % of rhodium powder, and 20 weight % of alumina powder were integrally overlaid on the porous solid electrolyte layer 33 with the electrode 5, as shown in FIG. 4. The integral body thus formed was baked at 1,450° C. in air, so as to produce an oxygen concentration detector.

A 5 V DC power source 26 was connected across the two terminals 11 of the heater 10 of the oxygen concentration detector thus produced, so as to apply an electric current thereto. In 30 seconds after the connection, the temperature of the solid electrolyte layer 1 reached 500° C. A bias current was applied to the electrode 5 from the positive (+) terminal of the DC power source 26 through a resistance 34 of 100 k$\Omega$, so as to keep the atmosphere of the electrode 5 as oxidizing. The oxygen concentration sensor thus formed was placed in an automobile exhaust gas of 300° C., and the electromotive force across the electrode 2 and the electrode 5 was measured by a voltmeter 27. It was 760 mV in an atmosphere with an air-fuel ratio $\lambda$ of 0.95, and 80 mV in an atmosphere with $\lambda = 1.05$. No deterioration was noticed even after 1,000 hours of continuous running in said exhaust gas.

As described in the foregoing, an electrochemical device according to the present invention has an excellent accuracy of electric output despite its simple construction, and its durability is very high without any deterioration of its electrolyte even after heating over a long period of time. Thus, the electrochemical device can be used as a sensor, a detector, or a controller of an electrodereaction-sensitive component of fluid, such as nitrogen, carbon dioxide, hydrogen, sodium, and the like. Especially, as a sensor of oxygen concentration of the exhaust gas from an internal combustion engine, the electrochemical device of the invention has advantage in that it accurately detects the oxygen concentration in the exhaust gas even immediately after the start of the engine or even in the case of low-temperature exhaust gas during low-speed running of the engine. Thus, the invention contributes greatly to the industry.

Although the invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An electrochemical device, comprising an electrochemical cell having at least one pair of electrodes disposed in contact with a solid electrolyte, a heater layer having a heater embedded in a ceramic layer having substantially the same coefficient of thermal expansion as that of said solid electrolyte, and a high electric resistance ceramic layer spread substantially over an entire span between said electrochemical cell and said heater layer.

2. An electrochemical device as set forth in claim 1, wherein said high electric resistance ceramic comprises a material selected from the group consisting of alumina and spinel.

3. An electrochemical device as set forth in claim 1, wherein said solid electrolyte consists essentially of zirconia ($ZrO_2$).

4. An electrochemical device as set forth in claim 3, wherein said ceramic layer of said heater layer consists essentially of zirconia ($ZrO_2$).

5. An electrochemical device as set forth in claim 4, wherein said high electric resistance ceramic layer is porous.

6. An electrochemical device as forth in claim 4, wherein said ceramic layer of said heater layer includes a gap at an intermediate portion thereof between mutually facing portions of said heater.

7. An electrochemical device as set forth in claim 3, wherein said high electric resistance ceramic layer is porous.

8. An electrochemical device as forth in claim 3, wherein said ceramic layer of said heater layer includes a gap at an intermediate portion thereof between mutually facing portions of said heater.

9. An electrochemical device as set forth in claim 1, wherein said high electric resistance ceramic layer is porous.

10. An electrochemical device as forth in claim 9, wherein said ceramic layer of said heater layer includes a gap at an intermediate portion thereof between mutually facing portions of said heater.

11. An electrochemical device as forth in claim 1, wherein said ceramic layer of said heater layer includes a gap at an intermediate portion thereof between mutually facing portions of said heater.

12. An electrochemical device, comprising an electrochemical cell having at least one pair of electrodes disposed in contact with a solid electrolyte, a heater layer having a heater carried by a ceramic layer having substantially the same coefficient of thermal expansion as that of said solid electrolyte, and a high electric resistance ceramic layer spread substantially over an entire span between said electrochemical cell and said heater layer so as to be attached to both said electrochemical cell and said heater layer, wherein said ceramic layer of said heater layer prevents the heater from being exposed to a gas to be measured.

13. An electrochemical device as set forth in claim 12, wherein said high electric resistance ceramic layer comprises a material selected from the group consisting of alumina and spinel.

14. An electrochemical device as set forth in claim 12, wherein said solid electrolyte consists essentially of zirconia ($ZrO_2$).

15. An electrochemical device as set forth in claim 14, wherein said ceramic layer of said heater layer consists essentially of zirconia ($ZrO_2$).

16. An electrochemical device as set forth in claim 15, wherein said high electric resistance ceramic layer is porous.

17. An electrochemical device as forth in claim 15, wherein said ceramic layer of said heater layer includes a gap at an intermediate portion thereof between mutually facing portions of said heater.

18. An electrochemical device as set forth in claim 14, wherein said high electric resistance ceramic layer is porous.

19. An electrochemical device as forth in claim 14, wherein said ceramic layer of said heater layer includes a gap at an intermediate portion thereof between mutually facing portions of said heater.

20. An electrochemical device as set forth in claim 12, wherein said high electric resistance ceramic layer is porous.

21. An electrochemical device as forth in claim 20, wherein said ceramic layer of said heater layer includes a gap at an intermediate portion thereof between mutually facing portions of said heater.

22. An electrochemical device as forth in claim 12, wherein said ceramic layer of said heater layer includes a gap at an intermediate portion thereof between mutually facing portions of said heater.

23. An electrochemical device, comprising an electrochemical cell having at least one pair of electrodes disposed in contact with a solid electrolyte, a heater layer having a heater embedded in a ceramic layer having substantially the same coefficient of thermal expansion as that of said solid electrolyte, and a high electric resistance ceramic layer spread substantially over an entire span between said electrochemical cell and said heater layer, wherein said ceramic layer of said heater layer prevents the heater from being exposed to a gas to be measured.

* * * * *